United States Patent [19]

Robertson et al.

[11] Patent Number: 4,929,393

[45] Date of Patent: May 29, 1990

[54] 1,4-DISUBSTITUTED-2,3,5,6-TETRAHYDROXY-1,4-DIPHOSPHORINANES AND THEIR OXIDES OR SULFIDES

[75] Inventors: Allan J. Robertson, Ontario, Canada; James B. Gallivan, Norwalk, Conn.

[73] Assignee: Cyanamid Canada Inc., Willowdale, Canada

[21] Appl. No.: 409,919

[22] Filed: May 22, 1989

Related U.S. Application Data

[62] Division of Ser. No. 309,572, Feb. 13, 1989, Pat. No. 4,855,507.

[30] Foreign Application Priority Data

Mar. 28, 1988 [CA] Canada .................................... 562688

[51] Int. Cl.$^5$ .......................... B03D 1/02; C08K 5/53
[52] U.S. Cl. ..................................... 252/609; 252/601; 568/12; 568/15; 524/116; 524/129
[58] Field of Search ........................... 252/609; 568/12

[56] References Cited

U.S. PATENT DOCUMENTS

| | | | |
|---|---|---|---|
| 4,052,484 | 10/1977 | Schliebs | 568/12 |
| 4,080,385 | 3/1978 | Block | 568/12 |
| 4,579,956 | 4/1986 | Redmore | 252/609 |
| 4,623,687 | 10/1986 | Green | 252/609 |
| 4,855,507 | 8/1989 | Robertson et al. | 568/12 |

*Primary Examiner*—Matthew A. Thexton
*Assistant Examiner*—Joseph Anthony
*Attorney, Agent, or Firm*—Frank M. Van Riet

[57] ABSTRACT

Various 1,4-disubstituted-2,3,5,6-tetrohydroxy-1,4-diphosphorinanes, their oxides and sulfides, methods for the production thereof, and flame-retarded compositions of matter containing them, are disclosed.

7 Claims, No Drawings

1,4-DISUBSTITUTED-2,3,5,6-TETRAHYDROXY-1,4-DIPHOSPHORINANES AND THEIR OXIDES OR SULFIDES

This is a division of application Ser. No. 309,572, filed Feb. 13, 1989, now U.S. Pat. No. 4,855,507.

BACKGROUND OF THE INVENTION

The reaction of primary phosphines and aldehydes to give a variety of products depending upon the nature of the substituent of the primary phosphine, the type of aldehyde and the presence of acid, is known. For example, primary aromatic or aliphatic phosphines react with formaldehyde in the presence of aqueous hydrochloric acid to give hydroxymethylphosphonium salts (Angew Chem. 72 211 [1960]);

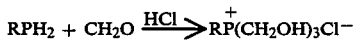

Phenyl phosphine and (a) acetaldehyde or (b) benzaldehyde, in the presence of hydrochloric acid, is reported to give a) phenyl bis (alpha-hydroxyethyl) phosphine and (b) phenyl bis(alpha-hydroxybenzyl)phosphine (CA 57:4692e [1962]);

while phenylphosphine and isobutyraldehyde, in hydrochloric acid solution, gives an alpha-hydroxyalkyl phosphine hydrochloride (Tetrahedron 18, 1231 [1962]).

Furthermore, phenyl phosphine when reacted with benzaldehyde will give three different products depending on the conditions and strength of the hydrochloric acid used,

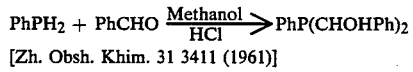
[Zh. Obsh. Khim. 31 3411 (1961)]

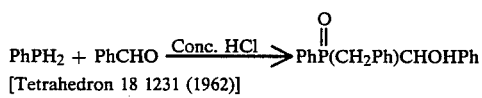
[Tetrahedron 18 1231 (1962)]

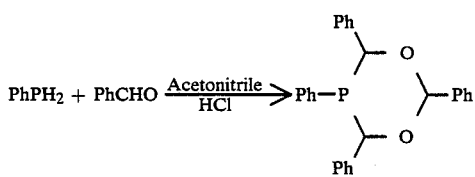
[Tetrahedron 18 1231 (1962)]

The reaction of phosphine and dialdehydes is reported to give spirocyclic phosphonium compounds of the formula;

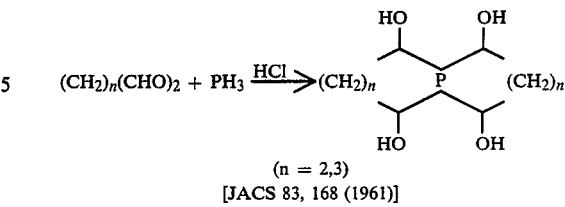
(n = 2,3)
[JACS 83, 168 (1961)]

The authors noted that "attempts to prepare an analogous spiran by reaction with glyoxal were unsuccessful".

The J.Org. Chem 35 (8) 2820 (1970) discloses the preparation of 2,5-dialkoxy-1,4-diphosphorinane-1,1,4,4-tetraphenyl, onium bromide, by the reaction of lithium diphenyl phosphide and chloroacetaldehyde, acetal followed by reaction with hydrogen bromide in acetic acid;

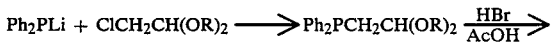

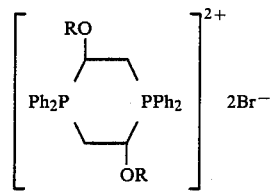
(R = CH$_3$, —CH$_2$CH$_3$)

In CA 88:5097d [Z. Chem. 17 (10) 365 (1977)] there is disclosed the preparation of 2,5-dihydroxy-1,1,4,4-tetraphenyl-1,4-diphosphorinonium dichloride by the reaction of the above phosphine with dilute hydrochloric acid;

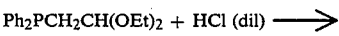

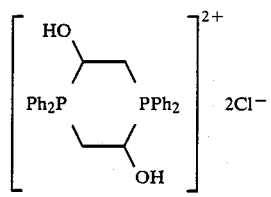

U.S. 3,206,496 (9/14/65) discloses the preparation of 1,4,diphosphorinonium salts by the reaction of a secondary phosphine and vinyl halides;

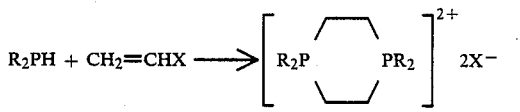

while U.S. 2,931,803 (4/5/60) teaches the preparation of fluorocarbon-containing 1,4-diphosphorinanes, 1,4-diiodides, prepared by the reaction of tetrafluoroethylene, elemental phosphorus, and iodine;

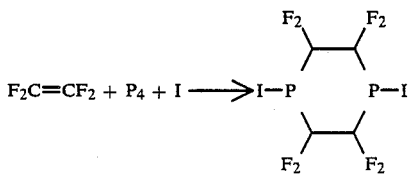

It is further disclosed that hydrolysis of above type heterocyclic followed by oxidation results in the formation of open-chain phosphonic acids. However, all above prior art diphosphorinanes are salts and are therefore totally different from the diphosphorinanes of the instant invention, and in addition are prepared by synthetic routes entirely different than the process of this invention.

DESCRIPTION OF THE INVENTION INCLUDING PREFERRED EMBODIMENTS

This invention relates to novel 1,4-disubstituted-2,3,5,6-tetrahydroxy-1,4-diphosphorinanes having the formula

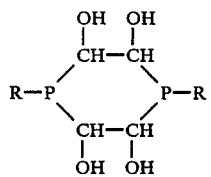

(I)

wherein R is a substituted or unsubstituted $C_1$–$C_{12}$ alkyl, $C_5$–$C_7$ cycloalkyl, $C_7$–$C_{12}$ aralkyl or $C_6$–$C_{12}$ aryl radical.

Among the preferred disubstituted tetrahydroxydiphosphorinanes conforming to Formula I are:

1,4-di-n-propyl-2,3,5,6-tetrahydroxy-1,4-diphosphorinane;
1,4-diisobutyl-2,3,5,6-tetrahydroxy-1,4-diphosphorinane;
1,4-bis(2-cyanoethyl)-2,3,5,6-tetrahydroxy-1,4-diphosphorinane
1,4-bis(phenethyl)-2,3,5,6-tetrahydroxy-1,4-diphosphorinane;
1,4-di-n-hexyl-2,3,5,6-tetrahydroxy-1,4-diphosphorinane;
1,4-di-sec-butyl-2,3,5,6-tetrahydroxy-1,4-diphosphorinane;
1,4-dicyclohexyl-2,3,5,6-tetrahydroxy-1,4-diphosphorinane;
1,4-bis(2,4,4-trimethylpentyl)-2,3,5,6-tetrahydroxy-1,4-diphosphorinane;
1,4-di-n-octyl-2,3,5,6-tetrahydroxy-1,4-diphosphorinane;
1,4-diphenyl-2,3,5,6-tetrahydroxy-1,4-diphosphorinane;
1,4-dinaphthyl-2,3,5,6-tetrahydroxy-1,4-diphosphorinane;

The disubstituted tetrahydroxydiphosphorinanes are readily prepared by the reaction of monosubstituted phosphines and glyoxal according to the equation:

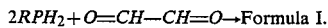

The reaction is carried out under an inert atmosphere using an aqueous solution of glyoxal, and a solution of the phosphine in a solvent miscible in the aqueous glyoxal solution. It is critical that the glyoxal be added to the phosphine because reverse addition results in an oxide mixture. The reaction is accomplished in the absence of external heating i.e., at ambient temperature since it is mildly exothermic. A slight molar excess of the aqueous glyoxal solution i.e., up to about 10%, is preferred. Nitrogen is the preferred inert atmosphere. The products crystallize from solution and can be recovered by filtration with purification, such as by washing. Suitable miscible solvents for the phosphine include alcohols such as ethanol, isopropanol, t-butanol, etc., tetrahydroguran; dioxane; dimethylformamide and the like. Although reagent grade change materials may be used to produce the novel phosphorinanes hereof, it is preferred that the charge materials be substantially free of any ingredient which will deleteriously interfere with the reaction. Thus, it is preferred that the glyoxal and the phosphine be substantially free of such ingredients as formaldehyde, acids, etc., however, small amounts thereof may be tolerated e.g., up to about 5.0%, by weight.

The disubstituted tetrahydroxydiphosphorinanes are useful as intermediates in the production of the dioxides and disulfides thereof, i.e., those compounds having the formula:

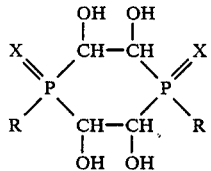

(II)

wherein R is as described above and X is oxygen or sulfur.

The compounds of Formula II are produced by reacting the compounds of Formula I, before or after separation and purification, as above, with hydrogen peroxide or elemental sulfur according to the equation:

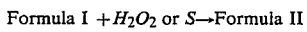

This reaction with the hydrogen peroxide or elemental sulfur is conducted in the presence of a hydroxylic solvent at a temperature ranging from about 60° C. to about 90° C. with cooling. Useful hydroxylic solvents include water, alcohols such as tert butanol isopropanol, ethanol, and the like. Among the preferred dioxides and disulfides falling with the scope of Formula II, include:

1,4-di-n-propyl-2,3,5,6-tetrahydroxy-1,4-diphosphorinane-1,4-dioxide;
1,4-di-n-propyl-2,3,5,6-tetrahydroxy-1,4-diphosphorinane-1,4-disulfide;
1,4-diisobutyl-2,3,5,6-tetrahydroxy-1,4-diphosphorinane-1,4-dioxide;
1,4-diisobutyl-2,3,5,6-tetrahydroxy-1,4-diphosphorinane-1,4-disulfide;
1,4-bis(2-cyanoethyl)-2,3,5,6-tetrahydroxy-1,4-diphosphorinane-1,4-dioxide;
1,4-bis(2-cyanoethyl)-2,3,5,6-tetrahydroxy-1,4-diphosphorinane-1,4-disulfide;
1,4-bis(phenethyl)-2,3,5,6-tetrahydroxy-1,4-diphosphorinane-1,4-dioxide;
1,4-bis(phenethyl)-2,3,5,6-tetrahydroxy-1,4-diphosphorinane-1,4-disulfide;
1,4-di-n-hexyl-2,3,5,6-tetrahydroxy-1,4-diphosphorinane-1,4-dioxide;

1,4-di-n-hexyl-2,3,5,6-tetrahydroxy-1,4-diphosphorinane-1,4-disulfide;
1,4-di-sec-butyl-2,3,5,6-tetrahydroxy-1,4-diphosphorinane-1,4-dioxide;
1,4-di-sec-butyl-2,3,5,6-tetrahydroxy-1,4-diphosphorinane-1,4-disulfide;
1,4-dicyclohexyl-2,3,5,6-tetrahydroxy-1,4-diphosphorinane-1,4-dioxide;
1,4-dicyclohexyl-2,3,5,6-tetrahydroxy-1,4-diphosphorinane-1,4-disulfide;
1,4-bis(2,4,4-trimethylpentyl)-2,3,5,6-tetrahydroxy-1,4-diphosphorinane-1,4-dioxide;
1,4-bis(2,4,4-trimethylpentyl)-2,3,5,6-tetrahydroxy-1,4-diphosphorinane-1,4-disulfide;
1,4-di-n-octyl-2,3,5,6-tetrahydroxy-1,4-diphosphorinane-1,4-dioxide;
1,4-di-n-octyl-2,3,5,6-tetrahydroxy-1,4-diphosphorinane-1,4-disulfide;
1,4-diphenyl-2,3,5,6-tetrahydroxy-1,4-diphosphorinane-1,4-dioxide;
1,4-diphenyl-2,3,5,6-tetrahydroxy-1,4-diphosphorinane-1,4-disulfide;
1,4-dinaphthyl-2,3,5,6-tetrahydroxy-1,4-diphosphorinane-1,4-dioxide;
1,4-dinaphthyl-2,3,5,6-tetrahydroxy-1,4-diphosphorinane-1,4-disulfide;

The products, i.e. the dioxides and disulfides are crystalline and are recovered in yields generally greater than 90%. They are high melting and have a low solubility in water.

The dioxides of Formula II find use as flame-retardants for polymeric materials and both the dioxides and disulfides have been found to be useful as mining reagents for the flotation of minerals e.g. as flotation agents or collectors for cassiterite, rare earth minerals and non-sulfide associated gold ores.

The dioxide flame-retardants may be incorporated into polymers to be flame-retarded by any known procedure such as, for example, Banbury mixing, two-roll mixing, extrusion, injection molding etc in flame-retarding quantities. Usually amounts ranging from about 2 to about 20%, by weight, based on the total weight of the polymer, may be used. Ofttimes the dioxide may be incorporated during the polymer production, such as by adding it to a monomer mixture undergoing polymerization.

The polymers into which the dioxides of the present invention may be incorporated include, but are not limited to, olefin polymers such as polyethylene, polypropylene; impact styrene polymers; nylon; polyphenylene oxide; impact styrene polymer modified polyphenylene oxide; polyethylene terephthalate; polyurethanes and the like.

Preferred flame-retardant polymer dioxides are those in which the substituent (R group of Formula II) is an alkyl group of 2-6 carbon atoms, cyanoalkyl, hydroxyalkyl, aryl or aralkyl (6 to 8 carbon atoms). Specific examples of preferred phosphine oxides include, but are not limited to, 1,4-di-n-propyl-2,3,5,6-tetrahydroxy-1,4-diphosphorinane-1,4-dioxide; 1,4-diisobutyl-2,1,4-dioxide, 1,4-bis(2-cyanoethyl)-2,3,5,6-tetrahydroxy-1,4-diphosphorinane-1,4-dioxide, 1,4-bis(phenethyl)-2,3,5,6-tetrahydroxy-1,4-diphosphorinane 1,4-dioxide and the like. The phosphine oxide flame-retardants may be used alone or in combination with other flame-retardants or synergists such as titanium dioxide, ammonium polyphosphate, melamine pyrophosphate, melamine, cyanoguanidine, urea, triaryl phosphates and the like. In the case of the flame-retarding of polyurethanes, the dioxides containing reactive functional groups may be also used as reactive intermediates to form polymeric materials containing the flame-retardant phosphine oxide moiety as part of the polymer backbone. Examples of phosphine oxides useful for the preparation of flame-retarded polyurethanes include but not limited to, 1,4-bis (3-hydroxypropyl)-2,3,5,6-tetrahydroxy-1,4-diphosphorinane-1,4-dioxide; 1,4-bis (3-aminopropyl)-2,3,5,6-tetrahydroxy-1,4-diphosphorinane-1,4-dioxide and the like.

To achieve flame-retardancy in polyurethanes, the reactive dioxides may be combined with the normally used polyols in concentrations in the range of about 2% to about 15%, by weight, based on the weight of the polyol, and reacted with isocyanates such as, for example, toluene diisocyanate (TDI) or methylene diphenyldiisocyanate (MDI) and the like to form the resultant flame-retarded polyurethane.

Various other additives may be added to the flame-retarded polymers such as plasticizers, pigments, fillers, stabilizers, i.e., antioxidants, etc., antistatic agents, dyes and the like.

As mentioned above, both the dioxides and disulfides of Formula II are useful as collectors in froth flotation procedures for beneficiating an ore containing minerals wherein liberation-sized particles of said ore are slurred in aqueous medium, said slurry is conditioned with effective amounts of a frothing agent and a mineral collector and the desired minerals are frothed by froth flotation procedures.

The following examples are set forth for purposes of illustration only and are not to be construed as limitations on the present invention except as set forth in the appended claims. All parts and percentages are by weight unless otherwise specified.

EXAMPLE 1

Preparation of 1,4-Diisobutyl-2,3,5,6-Tetrahydroxy-1,4-Diphosphorinane

In a suitable autoclave, equipped with mechanical stirring and external heating are added 200 parts of mono-isobutylphosphine (85%) and 300 parts of tetrahydrofuran, as solvent. With no external heating applied to the reactor, 275 parts of a 40% aqueous glyoxal solution are added with stirring at 20-25° C. The resultant solid product is filtered, and dried to give 276 parts (97% yield) of 1,4-diisobutyl-2,3,5,6-tetrahydroxy-1,4-diphosphorinane, m.p. 173-175° C.

EXAMPLE 2

Preparation of 1,4-Di-M-Hexyl-2,3,5,6-Tetrahydroxy-1,4-Diphosohorinane

In a suitable autoclave equipped as in Example 1, are added 200 parts of mono-n-hexylphosphine (93% purity) and 500 parts of isopropanol, as solvent. The mixture is heated to 60° C. and 240 parts of a 40% aqueous glyoxal solution are added. The reaction is allowed to proceed for one-hour and the solid product formed is filtered and dried to give 272 parts (98% yield) of 1,4-di-n-hexyl-2,3,5,6-tetrahydroxy-1,4-diphosphorinane, m.p. 140-147° C.

EXAMPLE 3

Preparation of 1,4-Di-M-Propyl-2,3,5,6-Tetrahydroxy-1,4-Diphosphorinane

Following the procedure of Example 1, mono-n-propylphosphine, in tetrahydrofuran, as solvent, is reacted with a 40% aqueous glyoxal solution, to give 1,4-di-n-propyl-2,3,5,6-tetrahydroxy-1,4-diphosphorinane, a solid melting at 131–133° C.

EXAMPLE 4

Preparation of 1,4-Di-Sec. Butyl-2,3,5,6-Tetrahydroxy-1,4-Diphosphorinane

Following the procedure of Example 1, 200 parts of mono-sec. butylphosphine in tetrahydrofuran, as solvent, is reacted with 336 parts of glyoxal (40% aqueous solution) to give, the product, 1,4-di-sec. butyl-2,3,5,6-tetrahydroxy-1,4-diphosphorinane, m.p. 145–180° C. in 79% yield.

EXAMPLE 5

Preparation of 1,4-Dineohexyl-2,3,5,6-Tetrahydroxy-1,4-Diphosphorinane

Following the procedure of Example 2, mononeohexyl phosphine (200 parts) in tetrahydrofuran, is reacted with 250 parts of glyoxal and 256 parts (90% yield) of 1,4-dineohexyl-2,3,5,6-tetrahydroxy-1,4-diphosphorinane, m.p. 186–210° C., are isolated.

EXAMPLE 6

Preparation of 1,4-Dicyclohexyl-2,3,5,6-Tetrahydroxy-1,4-Diphosohorinane

Following the procedure of Example 2, 150 parts of monocyclohexyl phosphine are reacted with 190 parts of 40% aqueous glyoxal solution to give 207 parts (92% yield) of 1,4-dicyclohexyl-2,3,5,6-tetrahydroxy-1,4-diphosphorinane, m.p. 182–215° C.

EXAMPLE 7

Preparation of 1,4-Bis (2,4;4-Trimethylpentyl)-2,3,5,6-Tetrahydroxy-1,4-Diphosphorinane Following the procedure of Example 1, 200 parts of mono-2,4,4-trimethylpentylphosphine (93% real) are reacted with 194 parts of glyoxal (40% aqueous solution) to give 235 parts (90% yield) of the solid product, 1,4-bis (2,4,4-trimethylpentyl)-2,3,5,6-tetrahydroxy-1,4-diphosphorinane, m.p. 130°–190° C.

EXAMPLE 8

Preparation of 1,4-Bis(n-Octyl)-2,3,5,6-Tetrahydroxy-1,4-Diphosohorinane

Following the procedure of Example 1, 200 parts of mono-n-octylphosphine is reacted with 194 parts of glyoxal to give 1,4-di-n-octyl-2,3,5,6-tetrahydroxy-1,4-diphosphorinane, a waxy solid.

EXAMPLES 9–12

Following the procedure of Example 1 various additional phosphorinanes are produced in accordance with the present invention. The compounds are set forth in Table I, below.

TABLE I

| Example | Phosphine | Product |
| --- | --- | --- |
| 9 | Phenethyl | 1,4-bis(phenethyl)-2,3,5,6-tetrahydroxy-1,4-diphosphorinane |
| 10 | 2-Cyanoethyl | 1,4-bis(2-cyanoethyl)-2,3,5,6-tetrahydroxy-1,4-diphosphorinane |
| 11 | Phenyl | 1,4-diphenyl-2,3,5,6-tetrahydroxy-1,4-diphosphorinane |
| 12 | p-Chlorophenyl | 1,4-bis(p-chlorophenyl)-2,3,5,6-tetrahydroxy-1,4-diphosphorinane |

EXAMPLES 13–24

Preparation of 1,4-dialkyl-2,3,5,6-Tetrahydroxy-1,4-Diphosphorinane-1,4-Dioxides The 1,4-dialkyl-2,3,5,6-tetrahydroxy-1,4-diphosphorinanes of Examples 1–12 are oxidized to the corresponding phosphine oxides by adding a slight excess (up to 10%) of hydrogen peroxide (30% aqueous solution) to a suspension the di phosphorinane in either water or isopropanol, at a temperature of 60–90° C. Cooling is applied as necessary, to maintain said temperature range. The yield and melting points of the resulting solid dioxides are set forth in Table II, below.

TABLE II

Preparation of 1,4-Substituted-2,3,5,6-Tetrahydroxy-1,4-Diphosohorinane-1,4-Dioxides

| Ex. No. | Substituent of Example No. | | m.p. (°C.) | Yield (%) |
| --- | --- | --- | --- | --- |
| 13 | n-Propyl | 3 | 249–252 | 42 |
| 14 | sec. Butyl | 4 | 255–262 | 76 |
| 15 | Isobutyl | 1 | 271–273 | 87 |
| 16 | n-Hexyl | 2 | 262–265 | 90 |
| 17 | Neohexyl | 5 | 271–225 | 88 |
| 18 | Cyclohexyl | 6 | 272–275 | 87 |
| 19 | 2,4,4-Trimethylpentyl | 7 | 230–232 | 79 |
| 20 | n-Octyl | 8 | 247–279 | 82 |
| 21 | Phenethyl | 9 | — | — |
| 22 | Phenyl | 11 | — | — |
| 23 | p-Chlorophenyl | 12 | — | — |
| 24 | 2-Cyanoethyl | 10 | — | — |

EXAMPLES 25–36

Preparation of 1,4-Substituted-2,3,5.6-Tetrahydroxy-1,4-diphosphorinane-1,4-Disulfides The 1,4-substituted-2,3,5,6-tetrahydroxy-1,4-diphosphorinanes of Examples 1–12 are converted to the corresponding sulfides of Formula II by adding a slight excess (up to 10%) of elemental sulfur to a suspension of the phosphine in either isopropanol or toluene at 60–90° C. for about 2 hours. The resulting solid phosphine sulfides are separated and isolated by filtration and drying. The yield and melting points of the products are set forth in Table III, below.

TABLE III

Preparation of 1,4-Substituted-2,3,5,6-Tetrahydroxy-1,4-diphosphorinane-1,4-Disulfides

| Ex. No. | Substituent | of Example No. | m.p. (°C.) | Yield (%) |
|---|---|---|---|---|
| 25 | Isobutyl | 1 | 243–244 | 95 |
| 26 | sec. butyl | 4 | 230–233 | 93 |
| 27 | n-Hexyl | 2 | 223–228 | 94 |
| 28 | Neohexyl | 5 | 258–260 | 97 |
| 29 | Cyclohexyl | 6 | 225–233 | 95 |
| 30 | 2,4,4-Tri-methylpentyl | 7 | 195–204 | 72 |
| 31 | n-Octyl | 8 | 219–222 | 75 |
| 32 | n-Propyl | 3 | 165–184 | 45 |
| 33 | p-Chlorophenyl | 12 | — | — |
| 34 | Phenethyl | 9 | — | — |
| 35 | Phenyl | 11 | — | — |
| 36 | 2-Cyanoethyl | 10 | — | — |

EXAMPLE 37

Evaluation of 1,4-Diisobutyl-2,3,5,6-Tetrahydroxy-1,4-Diphosphorinane-1,4-Dioxide As Flame Retardant in Polypropylene A blend of commercially available polypropylene, 0.1% of a commercially available antioxidant, and 20% of the dioxide of Example 15 is compounded on a two-roll plastic mill at 350° F. The resultant milled polymer is then compression molded into bars (5 inches ×0.5 inch ×0.125 inch) at 400–450° F. The compression molded bars are subjected to a vertical flammability test as follows: the polymer test specimen is clamped in a vertical position inside an exhaust hood at a distance of approximately 12 inches above the floor of the hood. With the exhaust in the off position, a small blue flame (0.75–1 inch) from a bunsen burner is applied to the bottom of the test specimen for 10 seconds. The flame is then removed and the time (in seconds) to flame extinguishment of the polymer sample is recorded. Also recorded is whether the sample shows flaming dripping. A total of five polymer test specimens are tested in accordance with the above flammability test. In all five samples, the flame is extinguished within one second after removal of the flame and no dripping is observed.

For comparative purposes, polypropylene test specimens which do not contain the above dioxide are also prepared as above, and tested by the same flammability test. In both of two test specimens tested, flaming with flaming dripping is observed for more than 30 seconds after removal of the ignition flame.

EXAMPLE 38

Evaluation of 1,4-Diisobutyl-2,3,5,6-Tetrahydroxy-1,4-Diphosphorinane-1,4-Dioxide/Ammonium Polyphosphate Combination as Flame Retardant in Polypropylene A blend of commercially available polypropylene containing 0.1% of a commercially available antioxidant, 10% of the compound of Example 15 and 10% of ammonium polyphosphate is compounded and compression molded, as in Example 37 above, into 5×0.5×0.125 inch bars. The bars are subjected to the flammability test method as in Example 37. A total of four test specimens is tested. In all cases, the flame of the polymer samples is extinguished within one second after removal of the ignition source and no dripping is observed. In order to determine their resistance of more stringent conditions, each of the four test specimens, above, is then subjected to an additional 10 second flame application immediately after flame extinguishment. It is found that in three of the four samples, the polymer flame extinguishes 6 seconds after removal of the second 10 second ignition source. The fourth sample burns for more than 10 seconds.

EXAMPLE 39

Evaluation of Flame Retardant Polypropylene Formulation Containing a Mixture of 1,4-Diisobutyl-2.3.5,6-Tetrahydroxy-1.4-Diphosphorinane-1.4-Dioxide and Titanium Dioxide Following the procedure described in Example 38, a polypropylene formulation containing 20% of the phosphorinane dioxide of Example 15 and 1% of titanium dioxide is milled and compression molded to give 5×0.5×0.125 inch bars. The bars are subjected to the vertical flammability outlined in Example 38. Five out of five test specimens tested, pass the first 10 second ignition with self-extinguishment time of less than one second and no dripping. A second ignition is applied to each specimen immediately following flame extinguishment and all five again pass the flammability test with one second or less self-extinguishment time and four out of five show no dripping.

EXAMPLE 40

Evaluation of Flame Retardant Polypropylene containing combination of 1.4-Diisobutyl-2.3,5,6-Tetrahydroxy-1,4-Diphosphorinane-1.4-Dioxide. Ammonium Polyphosphate and Titanium Dioxide Following the procedure described in Example 38 a polypropylene formulation containing 10% of the phosphorinane dioxide of example 15, 10% ammonium polyphosphate and 1% titanium dioxide is milled and compression molded to give 5×0.5×0.125 inch bars which are subjected to the same vertical flammability test. Five out of five test specimens tested pass the first 10-second ignition with a self-extinguishment time of one second or less and no dripping. Upon the application of a second 10-second ignition, again all five specimens pass the flammability test with a 5 second or less self-extinguishment time, and four out of five show no dripping.

EXAMPLES 41–49

Following the compounding and testing procedures of Example 37, different dioxides conforming to Formula II, above, are tested as flame-retardants. The results are set forth in Table IV, below.

TABLE IV

| Example | Dioxide of Example No. | | Passed Test |
|---|---|---|---|
| 41 | 13 | | yes |
| 42 | 17 | | yes |
| 43 | 18 | | yes |
| 44 | 16 | | yes |
| 45 | 14 | | yes |
| 46 | 21 | polyphenyleneoxide | yes |
| 47 | 24 | impact polystyrene | yes |
| 48 | 22 | polyethylene terephthalate | yes |
| 49 | 23 | polyethylene | yes |

EXAMPLES 50-53

A series of the compounds of the present invention is evaluated as flotation reagents in a sulfide ore containing lead, copper, zinc and iron. A mixture of 420 parts of the ore and the compound at a dosage rate of 50 part per ton of ore is ball-milled for 18 minutes at 66% solids. A suitable amount of cresylic acid (a frother) is added to the grinding mill and the ground pulp is transferred to a flotation cell, conditioned for two minutes at pH 8.5 and floated for five minutes using air at 5.5 liters per minute. The flotation concentrate is filtered, dried, weighed and analyzed for copper, lead, zinc and iron. The results are set forth in Table V, below.

TABLE V

| Example | Compound of Example No. | Percent Recovery | | | |
|---|---|---|---|---|---|
| | | Pb | Cu | Zn | Fe |
| 50 | 25 | 91.3 | 66.0 | 49.9 | 19.2 |
| 51 | 30 | 77.7 | 67.6 | 53.2 | 20.7 |
| 52 | 15 | 63.7 | 64.6 | 43.9 | 21.3 |
| 53 | 19 | 69.9 | 64.6 | 43.9 | 21.3 |

EXAMPLES 54-57

Following the procedure of Example 50-53, various additional compounds represented by Formula II, above are evaluated as collectors. In each instance, excellent recovery of the metals is achieved. The compounds evaluated are:

(54) 1,4-bis(phenethyl)-2,3,5,6-tetrahydroxy-1,4-phosphorinane disulfide.
(55) 1,4-bis(2-cyanoethyl)-2,3,5,6-tetrahydroxy-1-,4 phosphorinane disulfide.
(56) 1,4-diphenyl-2,3,5,6-tetrahydroxy-1,4-phosphorinane disulfide;
(57) 1,4-bis(p-chlorophenyl)-2,3,5,6-tetrahydroxy-1,4-phosphorinane disulfide.

We claim:

1. A composition of matter comprising a polymeric material containing a flame-retarding amount of the compound having the formula:

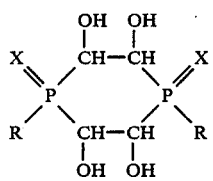

wherein R is a substituted or unsubstituted $C_1$–$C_{12}$ alkyl, $C_5$–$C_7$ cycloalkyl, $C_8$–$C_{12}$ aralkyl or $C_6$–$C_{12}$ aryl radical and X is oxygen or sulfuer.

2. A composition of matter according to claim 1 wherein R is alkyl.

3. A composition of matter according to claim 1 wherein R is isobutyl.

4. A composition of matter according to claim 1 wherein said polymer is produced from a monoethylenically unsaturated monomer.

5. A method of producing a flame-retarded composition of matter which comprises adding to a polymeric material a flame-retarding amount of a compound having the formula:

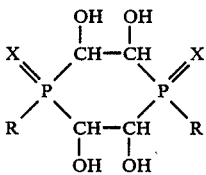

wherein R is a substituted or unsubstituted $C_1$–$C_{12}$ alkyl, $C_5$–$C_7$ cycloalkyl, $C_8$–$C_{12}$ aralkyl or $C_6$–$C_{12}$ aryl radical and X is oxygen or sulfuer.

6. A method according to claim 5 wherein R is alkyl.

7. A method according to claim 5 wherein R is isobutyl.

* * * * *